United States Patent [19]
Kardish et al.

[11] Patent Number: 5,648,047
[45] Date of Patent: Jul. 15, 1997

[54] DEVICE FOR COLORIMETRIC DETECTION OF EXPLOSIVES AND NARCOTICS

[76] Inventors: Nitza Kardish, 3 Shimshon, 64354; Israel Levy, 2 Kikar Masarick, 64351, both of Tel Aviv, Israel

[21] Appl. No.: 623,805

[22] Filed: Mar. 29, 1996

[51] Int. Cl.⁶ .......................... G01N 33/22; G01N 21/29
[52] U.S. Cl. .................. 422/56; 422/58; 422/61; 436/92; 436/110; 436/901
[58] Field of Search .................. 422/55, 56, 57, 422/58, 61; 436/44, 901, 110, 92

[56] References Cited

U.S. PATENT DOCUMENTS

| | | | |
|---|---|---|---|
| 3,607,079 | 9/1971 | Maxon et al. | 436/44 |
| 3,713,779 | 1/1973 | Sirago et al. | |
| 3,748,098 | 7/1973 | Dutch | |
| 3,915,639 | 10/1975 | Friedenberg | |
| 3,920,987 | 11/1975 | Anbar et al. | |
| 4,752,448 | 6/1988 | Wells et al. | |
| 4,771,005 | 9/1988 | Spiro | 436/93 |
| 4,788,039 | 11/1988 | Glattstein | 422/61 |
| 4,828,797 | 5/1989 | Zwarun et al. | |
| 4,866,439 | 9/1989 | Kraus | |
| 4,930,053 | 5/1990 | Fechtner | |
| 4,965,047 | 10/1990 | Hammond | |
| 4,981,785 | 1/1991 | Nayak | |
| 5,009,850 | 4/1991 | Bell | 422/58 X |
| 5,035,860 | 7/1991 | Kleingeld et al. | |
| 5,094,816 | 3/1992 | Ishizaka et al. | |
| 5,138,889 | 8/1992 | Conrad | |
| 5,238,649 | 8/1993 | Nason | 422/58 |
| 5,278,418 | 1/1994 | Broadhurst | |
| 5,296,380 | 3/1994 | Margalit | |
| 5,345,809 | 9/1994 | Corrigan et al. | |
| 5,442,271 | 8/1995 | Chen et al. | |
| 5,457,054 | 10/1995 | Geisinger et al. | 436/92 |
| 5,476,794 | 12/1995 | O'Brien et al. | |

FOREIGN PATENT DOCUMENTS

| | | | |
|---|---|---|---|
| 522792 | 1/1977 | Japan | 436/44 |
| 5582964 | 6/1980 | Japan | 436/44 |

OTHER PUBLICATIONS

Fisher Scientific Catalog, p. 841 (1988).

*Primary Examiner*—Jeffrey Snay
*Attorney, Agent, or Firm*—Mark M. Friedman

[57] ABSTRACT

A hand-held device for rapid colorimertic detection of explosives, narcotics, and other chemicals which can be accurately operated by non-skilled personnel and perform numerous tests in a quick sequential manner without exposing a user to hazardous reagents and without exposing sensitive reagents to deteriorating environmental conditions, the device comprising (a) a housing for handling and using the device, the housing including a sampling area an a testing area; (b) a roll of substrate for sampling materials suspected as including the chemical; (b) a feeding reel being rotatably connected to the housing, the feeding reel being for accommodating the roll of substrate; (c) at least one container for accommodating at least one detecting reagent, the at least one detecting reagent is for the colorimetric detection of the chemical; and (d) at least one dispensing mechanism for dispensing a predetermined volume of the at least one reagent onto the substrate at the testing area.

27 Claims, 1 Drawing Sheet

DEVICE FOR COLORIMETRIC DETECTION OF EXPLOSIVES AND NARCOTICS

FIELD AND BACKGROUND OF THE INVENTION

The present invention relates to a device for color detection of chemicals and, more particularly, to a hand-held device for rapid colorimetric detection of explosives, narcotics and other chemicals, which device can be accurately operated by non-skilled personnel and can perform numerous tests in a quick sequential manner without exposing a user to hazardous reagents and without exposing sensitive reagents to deteriorating environmental conditions.

Detection of minute quantifies of chemicals on objects may be affected in two alternative strategies.

The first strategy involves sampling an air sample from near the object and chemically analyzing the chemicals present in the air sample using methods such as for example mass spectroscopy, gas chromatography, electron capture, etc. This procedure although quantitative is complicated since the analyzing apparatuses are complex, expensive, in many cases not portable and require power supply. Furthermore, some chemicals, those characterized by low vapor pressure such as for example plastic explosives, are some times difficult for detection using these methods. In these cases sampling of the surface of the object itself is required.

The second strategy involves sampling the surface of the object using a collecting substrate (e.g., a paper or a cloth materiel) and analyzing the collected sample with reagents applied onto the collecting substrate to generate a specifying color reaction when a target chemical is present in the sampled sample.

Principally, the later strategy is more suitable for operation by non-skilled personnel such as guards, policemen and soldiers in airports, border crossings, bus stations and buses, for a simple and quick detection of explosives and/or narcotics.

Nevertheless, sequentially adding reagents onto the collecting substrate for color detection of chemicals suspected to be present on the substrate after sampling is in many cases cumbersome and thus inconvenient to execute under field conditions.

Furthermore, as some of the reagents employed are either sensitive to environmental influences (e.g., light, air, dust, etc.) under which they deteriorate fast, or harmful and thus dangerous to the user (e.g., organic solvents including reagents), thus sampling and color detecting chemicals may become inaccurate and dangerous to the user, respectively.

As terror and narcotic drugs become an ever growing problem worldwide, there is a widely recognized need for, and it would be highly advantageous to have, a hand held device for colorimetric detection of chemicals such as explosives and narcotics, which device can be accurately operated by non-skilled personnel and can perform numerous tests in a quick sequential manner without exposing the user to hazardous reagents and without exposing sensitive reagents to deteriorating environmental conditions.

SUMMARY OF THE INVENTION

According to the present invention there is provided a hand-held device for rapid colorimertic detection of explosives, narcotics and other chemicals, which device can be accurately operated by non-skilled personnel and can perform numerous tests in a quick sequential manner without exposing a user to hazardous reagents and without exposing sensitive reagents to deteriorating environmental conditions.

According to further features in preferred embodiments of the invention described below, the device comprising (a) a housing having means for handling and using the device, the housing including a sampling area an a testing area; (b) a roll of substrate for sampling materials suspected as including the chemical; (c) a feeding reel being rotatably connected to the housing, the feeding reel being for accommodating the roll of substrate; (d) at least one container for accommodating at least one detecting reagent, the at least one detecting reagent is for the colorimetric detection of the chemical; and (e) at least one dispensing mechanism for dispensing a predetermined volume of the at least one reagent onto the substrate at the testing area.

According to still further features in the described preferred embodiments the device further comprising (f) a take-up reel being rotatably connected to the housing for advancing the substrate along the sampling area into the testing area.

According to still further features in the described preferred embodiments the housing includes a base and a body.

According to still further features in the described preferred embodiments the base and body are separatable one from the other.

According to still further features in the described preferred embodiments the base and body are rotatable one relative to the other.

According to still further features in the described preferred embodiments each of the one containers is continued by a robe for directing the each of the at least one reagent to the testing area.

According to still further features in the described preferred embodiments each of the tubes has a diameter permitting formation of a capillary effect for effecting the dispensing of the predetermined volume of the at least one reagent onto the substrate at the testing area.

According to still further features in the described preferred embodiments the testing area and the second real are in the housing, the housing includes a transparent region for permitting a user to view the testing area.

According to still further features in the described preferred embodiments the means for handling and using the device include a handle.

According to still further features in the described preferred embodiments the substrate is selected from the group consisting of a paper, a cloth and a synthetic membrane.

According to still further features in the described preferred embodiments the substrate is supplemented with an adsorbing agent for increased sampling capabilities of the suspected material.

According to still further features in the described preferred embodiments the substrate is supplemented with a supporting film.

According to still further features in the described preferred embodiments each of the at least one containers is made of an elastic material.

According to still further features in the described preferred embodiments at least one of the at least one containers contains at least one breakable ample, each of the at least one ampoules contains one of the at least one reagents, the ampoule is for providing the reagent with a longer shelf life.

According to still further features in the described preferred embodiments the number of containers is selected from the group consisting of one, two three and four, each of the containers has a corresponding dispensing mechanism.

According to still further features in the described preferred embodiments each of the dispensing mechanisms is formed as a lever system and includes a dispensing button.

According to still further features in the described preferred embodiments the feeding reel includes a biasing mechanism for keeping the advancing of the substrate along the sampling area smooth.

According to still further features in the described preferred embodiments the take-up reel includes a ratchet mechanism for stepwise advancing the substrate along the sampling and testing areas.

According to still further features in the described preferred embodiments the housing includes at least one roller for keeping the advancing of the substrate along the sampling area smooth.

According to still further features in the described preferred embodiments the housing includes a cover for protecting the substrate.

According to still further features in the described preferred embodiments the sampling area is formed as a tip.

According to still further features in the described preferred embodiments the chemical is selected from the group consisting of an explosive chemical and a narcotic chemical.

According to still further features in the described preferred embodiments the explosive chemical includes a chemical moiety selected from the group consisting of a nitromatic moiety, organic nitrate moiety, nitramine moiety, inorganic nitrate moiety, chlorate moiety and bromate moiety.

According to still further features in the described preferred embodiments the narcotic chemical includes a chemical selected from the group consisting of cannabinoids, cocainoids and heroinoids.

According to still further features in the described preferred embodiments the chemical is an explosive chemical, the at least one reagent is selected from the group consisting of alkaline solution of a diazotizable aminoaromatic azo-dye precursor, an acidic solution containing a nitrate to nitrite ion reducing agent and a diazo-coupler, a zinc powder suspended in a liquid, an aniline salt in a homogenous strongly acidic solution including a water-miscible organic solvent, a 2.5–20% V/V of tetra alkyl phosphonium hydroxide in a solvent including at least 60% V/V DMSO and about 30% V/V methanol or water, and a 2.5–20% V/V of tetra alkyl ammonium hydroxide in a solvent including at least 60% V/V DMSO and about 30% V/V methanol or water.

According to still further features in the described preferred embodiments the chemical is a narcotic chemical, the at least one reagent is selected from the group consisting of a cocaine visualization reagent, heroin visualization reagent, tetrahydrocannabinol visualization reagent.

According to still further features in the described preferred embodiments the chemical is used during preparation, treatment or storage of narcotic chemicals.

According to still further features in the described preferred embodiments the chemical used during preparation, treatment or storage of narcotic chemicals is selected from the group consisting of organic bases and acetic acid.

The present invention successfully addresses the shortcomings of the presently known configurations by providing a device for colorimertic detection of various chemicals, which can be accurately operated by non-skilled personnel and can perform numerous tests in a quick sequential manner without exposing a user to hazardous reagents and without exposing sensitive reagents to deteriorating environmental conditions.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
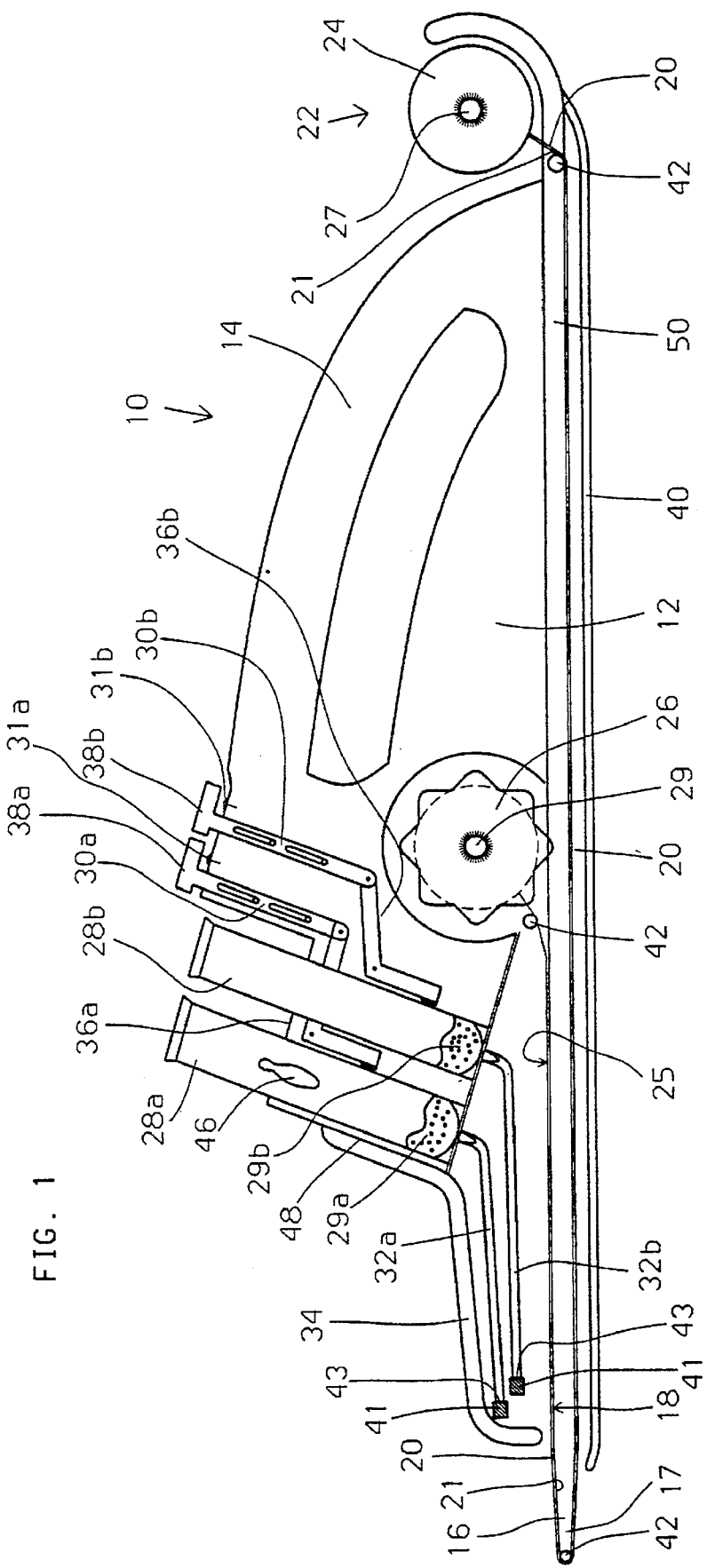
FIG. 1 is a cross section view of an illustrative device for colorimetric detection of chemicals according to the teachings of the present invention.

The present invention is of hand-held device for rapid colorimetric detection of explosives, narcotics and other chemicals, which can be used by non-skilled personnel for accurate detection of presence of chemicals in a test sample. Specifically, the present invention can be used to perform numerous tests in a quick sequential manner without exposing a user to hazardous reagents and without exposing sensitive reagents to deteriorating environmental conditions.

The principles and operation of a device for colorimetric detection of chemicals according to the present invention may be better understood with reference to the drawing and accompanying descriptions.

Methods for colorimetric detection of chemicals, although to a great extent not quantitative, are simple to execute, fairly sensitive and are therefore used qualitatively both in various scientific fields (e.g., biology) and medicine and in other fields where non-skilled personnel are to execute the method (e.g., pregnancy test).

Therefore, methods for colorimetric detection of explosives, narcotic drugs and other chemicals were developed to be used under field conditions by law enforcing personnel, security guards, etc.

U.S. Pat. No. 5,296,380 to Margalit which is incorporated by reference as if fully set forth herein discloses a method and kit for detecting explosives. The method by Margalit is directed at detecting particular classes of explosives in a color reaction. According to this method a sample from a suspected source is subjected serially to types of reagents, wherein each reagent is directed at color detection of a different type of explosive, thus reagents after the first being applied to the sample only if no color has been obtained in the preceding test. The first reagent is an alkaline solution of a diazotizable aminoaromatic azo-dye precursor, which detects nitromatic explosives. The second reagent is a strongly acidic reagent containing a nitrate to nitrite ion reducing agent and a diazo-coupler, which detects organic nitrates and nitramines. The third reagent is zinc powder suspended in a liquid, which detects inorganic nitrates. Whereas, the fourth reagent is an aniline salt in a homogenous strongly acidic solution including a water-miscible organic solvent, which detects chlorates and bromates. Thus, according to this invention at least one, yet in many cases four reagents are to be contacted with an examined sample for explosives detection.

U.S. Pat. No. 4,788,039 to Glattstein which is incorporated by reference as if fully set forth herein discloses a different method and kit for detection of explosives. According to Glattstein, two reagents are used for color detection of explosives. The first reagent includes 2.5–20% V/V of tetra alkyl ammonium or phosphonium hydroxide in a solvent comprising at least 60% V/V dimethylsulfoxide (DMSO)

and about 30% V/V methanol or water. The second reagent includes a diazotization compound and a coupling compound of a Griess reagent pair.

U.S. Pat. Nos. 4,771,005 to Spiro, 5,457,054 to Geisinger et at., and 4,840,912 to Glattstein, all are incorporated by reference as if fully set forth herein, disclose reagents, methods and test kits for colorimetric detection of various types of narcotic drugs such as cannabinoids, cocaine and heroin.

Nevertheless, all these methods involve contacting reagent(s) with a tested sample in a manual fashion which is cumbersome, inaccurate and in some cases harmful to the user or deteriorating to the reagents themselves.

Referring now to the drawing, FIG. 1 illustrates a handheld device for color detection of chemicals according to the present invention, referred to hereinbelow as device 10. As will be explained in greater details below, device 10 performs all functions associated with color detection of chemicals, collectively rendering device 10 highly suitable for repetitive sampling and detection of desired chemicals sampled from various objects such as but not limited to suitcases, bags, etc., and people, under field conditions by non-skilled personnel, while at the same time device 10 provide means for protecting users from hazards associated with contacting or inhaling various detection reagents (e.g., ones including organic solvents, strong acids or bases, etc.) and means for protecting sensitive reagents from environmental effects such as light, air, etc., if so required.

Thus, as shown in FIG. 1, device 10 includes a housing 12. Housing 12 has means for handling and using device 10, formed as handle 14 in the example of FIG. 1. Housing 12 further includes a sampling area 16 an a testing area 18, whereat sampling of materials suspected as including a chemical and colorimetrically testing for the presence or absence of the chemical, respectively, take place, as is further described in detail hereinbelow. Preferably, sampling area 16 is formed as a tip 17 which is better suited for sampling as described.

Device 10 further includes a roll 22 of substrate 20 for sampling the material(s) suspected as including the chemical. Substrate 20 is selected such that it has a surface suitable for sampling materials from objects such as suitcases, bags, skin of people, etc. Suitable substrates include, but are not limited to, paper, cloth and synthetic membrane. In a preferred embodiment, substrate 20 is supplemented with an adsorbing agent (e.g., glue) for increased sampling capabilities of the suspected material. Roll 22 of substrate 20 is engaged by a feeding reel 24 which is rotatably connected to housing 12. In another preferred embodiment, substrate 20 is supported by a supporting film 21 which increases its resistance. Suitable supporting films include but are not limited to synthetic polymers such as plastic. As will be described shortly, prior to sampling, reel 24 feeds sampling area 16 with fresh (i.e., yet unused) substrate 20. Preferably, feeding reel 24 includes a biasing mechanism (e.g., a spring) 27 ensuring that advancing substrate 20 along sampling area 16 is smooth and that substrate 20 maintains a predetermined tension and is not loose.

Used segments 25 of substrate 20 are preferably engaged by a take-up reel 26 which is rotatably connected to housing 12, preferably within housing 12. Take-up reel 26 is for advancing substrate 20 and thus the sampled material from sampling area 16 into testing area 18. Preferably take-up reel 26 includes a ratchet mechanism 29 for stepwise advancing substrate 20 along sampling 16 and testing 18 areas. Biasing mechanism 27 and ratchet mechanism 29 collectively act to ensure that a fresh region of substrate 20 is used for each independent sampling and testing.

Nevertheless, as will be appreciated by one ordinarily skilled in the art, device 10 is operative also without take-up reel 26, wherein manually pulling substrate 20 is used to advance substrate 20 as described.

Device 10, further includes at least one, preferably two, more preferably four container 28 (two are shown in FIG. 1, referred to as 28a and 28b) for accommodating at least one detecting reagent 29a and 29b, respectively, each of reagents 29a and 29b is for a colorimetric detection of a specific chemical or a specific family of chemicals sharing a mutual detectable chemical moiety.

In a preferred embodiment, each of containers 28 is made of an elastic and transparent (unless the reagent contained in it is light sensitive) material. Providing containers 28 transparent ensures that depletion of reagents is easily detected by the user of device 10.

Device 10 further includes at least one dispensing mechanism 30a and 30b for dispensing a predetermined volume of reagents 29a an 29b, respectively, onto substrate 20 at testing area 18.

In a preferred embodiment, each of containers 28 is continued by a tube 32a and 32b, respectively, for directing reagents 29 to testing area 18. Each of tubes 32 preferably has a diameter permitting the formation of a capillary effect for effecting the dispensing of the predetermined volume of reagents 29 onto substrate 20 at testing area 18. By having a capillary effect, tubes 32 ensure that constant volume of liquids (i.e., one drop from each reagent) is delivered onto testing area 18. The quantity (i.e., volume) of liquid in a given drop is a complex function of the diameter of tubes 32, its material of made and the type of liquid. Yet, one can experimentally select tubes 32 permitting application of a particular quantity of reagents 29 onto substrate 20 at testing area 18.

In yet another preferred embodiment, testing area 18 and take-up real 26 are sequestered within housing 12. Thus, a user is not exposed to hazardous effects of reagents 29, should they have any. In this case housing 12 preferably includes a transparent region or a movable cover 34 for permitting the user to view testing area 18.

In yet another preferred embodiment, each of dispensing mechanisms 32 is formed as a lever system 36 and includes a dispensing button 38. Preferably, dispensing mechanism 32 is equipped with at least one button stopper 31, shown in FIG. 1 in the form of knobs 31 implemented onto housing 12 underneath buttons 38. Any type of dispensing mechanism is suitable for the inventive device 10. Thus, for example, as will be appreciated by one ordinarily skilled in the art, dispensing mechanisms 32 may alternatively be implemented directly onto containers 28 (not shown), in a fashion similar for example to the implementation of a dispensing mechanism of a medical syringe, or the like. In this case, a unidirectional valve 41 may be implemented at the dripping end 43 of each of tubes 32, to prevent air from entering containers 28, if so required.

In yet another preferred embodiment, housing 12 further includes a cover 40 for protecting segments of substrate 20 which are unrolled from roll 22, yet are not in immediate use.

In yet another preferred embodiment, housing 12 further includes at least one roller 42 (three are shown in FIG. 1) for further keeping advancing of substrate 20 along sampling 16 and testing 18 areas smooth. As will be appreciated by one ordinarily skilled in the art, the number and location of roller(s) 42 may vary depending on the specific construction of device 10.

In yet another preferred embodiment, containers 32 are prepacked with suitable reagents 29 and are implemented into accommodating means 48 formed in housing 12. When any of reagents 29 is depleted, e.g., after ca. 100 tests, the empty container is replaced by a fresh one.

Yet, depending on the reagent, reusable containers are also possible for implementation in device 10.

Likewise, when device 10 is depleted from fresh substrate 20, a new roll 22 is placed onto feeding 24 and take-up 26 reels. To this end, housing 12 is preferably constructed from at least two separatable or rotatable parts, e.g., a base 50 and a body 52, which can be either separated from one another or rotated one relative to the other, respectively.

The operation of device 10, according to its preferred embodiments, is as follows. When a user wishes to test a material suspected as including a chemical such as explosive or narcotic, etc., the user first ensures that a clean segment of substrate 20 is located at sampling area 16 by rolling substrate 20 around take-up reel 26. Then, aided by tip 17, the user samples a surface of a tested object by wiping the surface with tip 17. At this point sampling is completed.

After sampling, the user, again aided by take-up reel 26, further rolls substrate 20 until the segment of substrate 20 that was previously used for sampling is located at testing area 18.

Since the actual distance between sampling area 16 and testing area 18 is constant for a given device 10, ratchet mechanism 29 is preferably employed to ensure that the appropriate segment of surface 20 is positioned at testing area 18. At this stage, ratchet mechanism 29 of take-up reel 26 and biasing mechanism 27 of feeding reel 24 ensure that surface 20 is still until the colorimetric test is completed.

After the positioning of the segment of substrate 20 containing the sampled material at testing area 18, the user activates dispensing mechanisms 28, at a predetermined order, thus a drop having a predetermined volume, formed due to the flexibility of containers 28 and the capillary effect of tubes 32, of each of reagents 29, is contacted with the sampled material at a predetermined sequential order, permitting a colorimetric reaction to take place provided that the sampled material contains the tested chemical. The color thus formed or does not form on substrate 20 is viewed by the user through transparent region or a movable cover 34 and the presence or absence of the tested chemical is determined.

It will be appreciated by one skilled in the art, that according to the preferred embodiments as described hereinabove, reagent(s) 29 are sequestered within housing 12, i.e., testing area 18 and take-up reel 26 are both preferably within housing 12, therefore the user is protected from hazardous effects associated with contacting or inhaling any of the chemicals used in the colorimetric detection.

As mentioned in U.S. Pat No. 5,296,380 some reagents are quickly deteriorated when contacted with air. Therefore, if such sensitive reagents are of concern, they may be kept sealed in a breakable ampoule 46 encaged within container 28, which ampoule 46 is broken prior to use, providing reagent(s) 29 with a longer shelf life.

Any chemical having a matching colorimetric detecting reagent can be detected using device 10 of the present invention. Yet, device 10 is highly suitable for efficient, quick and safe detection of explosive and narcotic chemicals, under field conditions even when device 10 is operated by non-skilled personnel.

Thus, device 10 can be used to detect residual amounts of explosive containing chemicals having chemical moieties such as but not limited to a nitromatic moiety, organic nitrate moiety, nitramine moiety, inorganic nitrate moiety, chlorate moiety and/or bromate moiety.

Furthermore, device 10 can be used to detect residual amounts of narcotic drugs such as but not limited to cannabinoids, cocainoids and/or heroinoids, or chemicals associated with their preparation storage, shipping and/or street distribution (e.g., organic bases and acetic acid).

Various types of reagents aimed at colorimetric detection of various explosives can thus be contained in containers 32. These include but are not limited to (i) alkaline solution of a diazotizable aminoaromatic azo-dye precursor; (ii) an acidic solution containing a nitrate to nitrite ion reducing agent and a diazo-coupler; (iii) a zinc powder suspended in a liquid; (iv) an aniline salt in a homogenous strongly acidic solution including a water-miscible organic solvent; (v) a 2.5–20% V/V of tetra alkyl phosphonium hydroxide in a solvent including at least 60% V/V DMSO and about 30% V/V methanol or water; and/or (vi) a 2.5–20% V/V of tetra alkyl ammonium hydroxide in a solvent including at least 60% V/V DMSO and about 30% V/V methanol or water.

Various types of reagents aimed at colorimetric detection of various narcotics can alternatively be contained in containers 32. These include but are not limited to a cocaine visualization reagent, heroin visualization reagent, and/or tetrahydrocannabinol visualization reagent, all as described in U.S. Pat. Nos. 4,771,005 to Spiro, 5,457,054 to Geisinger et al., and 4,840,912 to Glattstein.

The device for colorimetric detection of chemicals such as explosives and narcotics according to the present invention has the following advantages. It is a hand-held device which does nor require a power source for its operation. It can be used for rapid and repetitive colorimetric detection of explosives, narcotics and other chemicals. It can be easily and accurately operated by non-skilled personnel. It can be used to perform numerous tests in a quick sequential manner without exposing the user to hazardous reagents and without exposing sensitive reagents to deteriorating environmental conditions.

While the invention has been described with respect to a limited number of embodiments, it will be appreciated that many variations, modifications and other applications of the invention may be made.

What is claimed is:

1. A hand-held device for colorimetric detection of a chemical obtained by sampling a surface of an object for enabling a large number of tests to be successively performed, the hand-held device comprising:

(a) a housing having means for handling and using the hand-held device, said housing including a sapling area and a testing area, said sampling area being formed as a tip, said tip being dimensioned and positioned for permitting the sampling of the surface of the object by wiping the surface of the object;

(b) a roll of substrate for sampling materials suspected as including the chemical from the surface of the object;

(c) a feeding reel being rotatably connected to said housing, said feeding reel accommodating said roll of substrate, said substrate extending at least from said feeding reel to said tip and said testing area;

(d) at least one container for accommodating at least one detecting reagent, wherein said at least one detecting reagent is for the colorimetric detection of the chemical; and (e) at least one dispensing mechanism for dispensing a predetermined volume of said at least one reagent onto said substrate at said testing area.

2. A device as in claim 1, wherein said means for handling and using the device include a handle.

3. A device as in claim 1, wherein said substrate is selected from the group consisting of a paper, a cloth and a synthetic membrane.

4. A device as in claim 1, wherein said substrate is supplemented with an adsorbing agent for increased sampling capabilities of said suspected material.

5. A device as in claim 1, wherein said substrate is supplemented with a supporting film.

6. A device as in claim 1, wherein each of said at least one containers is made of an elastic material.

7. A device as in claim 1, wherein at least one of said at least one containers contains at least one breakable ampoule, each of said at least one ampoules contains one of said at least one reagents.

8. A device as in claim 1, wherein the number of containers is selected from the group consisting of one, two, three and four, and each of said containers has a corresponding dispensing mechanism.

9. A device as in claim 1, wherein each of said dispensing mechanisms is formed as a lever system and includes a dispensing button.

10. A device as in claim 1, wherein said feeding reel includes a biasing mechanism for keeping said advancing of said substrate along said sampling area smooth.

11. A device as in claim 1, wherein said housing includes at least one roller for keeping said advancing of said substrate along said sampling area smooth.

12. A device as in claim 1, wherein said housing includes a cover for protecting said substrate.

13. A device as in claim 1, wherein the chemical is an explosive chemical, said at least one reagent is selected from the group consisting of alkaline solution of a diazotizable aminoaromatic azo-dye precursor, an acidic solution containing a nitrate to nitrite ion reducing agent and a diazocoupler, a zinc powder suspended in a liquid, an aniline salt in a homogenous strongly acidic solution including a water-miscible organic solvent, a 2.5–20% V/V of tetra alkyl phosphonium hydroxide in a solvent including at least 60% V/V dimethyl sulfoxide and about 30% V/V methanol or water, and a 2.5–20% V/V of tetra alkyl ammonium hydroxide in a solvent including at least 60% V/V dimethyl sulfoxide and about 30% V/V methanol or water.

14. A device as in claim 1, wherein the chemical is a narcotic chemical, said at least one reagent is selected from the group consisting of a cocaine visualization reagent, heroin visualization reagent, tetrahydrocannabinol visualization reagent.

15. A device as in claim 1, further comprising:
(f) a take-up reel being rotatably connected to said housing for advancing said substrate along said sampling area into said testing area.

16. A device as in claim 15, wherein said testing area and said take-up real are in said housing, said housing includes a transparent region for permitting a user to view said testing area.

17. A device as in claim 15, wherein said take-up reel includes a ratchet mechanism for stepwise advancing said substrate along said sampling and testing areas.

18. A device as in claim 1, wherein said housing includes a base and a body.

19. A device as in claim 18, wherein said base and body are separatable one from the other.

20. A device as in claim 18, wherein said base and body are rotatable one relative to the other.

21. A device as in claim 1, wherein each of said at least one containers is contained by a tube for directing said each of said at least one reagent to said testing area.

22. A device as in claim 21, wherein each of said tubes has a diameter permitting formation of a capillary effect for effecting said dispensing of said predetermined volume of said at least one reagent onto said substrate at said testing area.

23. A device as in claim 1, wherein said chemical is selected from the group consisting of an explosive chemical and a narcotic chemical.

24. A device as in claim 23, wherein said explosive chemical includes a chemical moiety selected from the group consisting of a nitromatic moiety, organic nitrate moiety, nitramine moiety, inorganic nitrate moiety, chlorate moiety and bromate moiety.

25. A device as in claim 23, wherein said narcotic chemical includes a chemical selected from the group consisting of cannabinoids, cocainoids and heroinoids.

26. A device as in claim 1, wherein the chemical is used during preparation, treatment or storage of narcotic chemicals.

27. A device as in claim 26, wherein the chemical used during preparation, treatment or storage of narcotic chemicals is selected from the group consisting of organic bases and acetic acid.

* * * * *